(12) United States Patent
Eddaoudi et al.

(10) Patent No.: US 10,759,724 B2
(45) Date of Patent: Sep. 1, 2020

(54) ZEOLITE-LIKE METAL-ORGANIC FRAMEWORKS WITH ANA TOPOLOGY

(71) Applicant: King Abdullah University of Science and Technology, Thuwal (SA)

(72) Inventors: Mohamed Eddaoudi, Thuwal (SA); Youssef Belmabkhout, Thuwal (SA); Mohamed Infas Haja Mohideen, Thuwal (SA); Karim Adil, Thuwal (SA); Prashant M. Bhatt, Thuwal (SA); Osama Shekhah, Thuwal (SA); Valeriya Chernikova, Thuwal (SA)

(73) Assignee: KING ABDULLAH UNIVERSITY OF SCIENCE AND TECHNOLOGY, Thuwal (SA)

(*) Notice: Subject to any disclaimer, the term of this patent is extended or adjusted under 35 U.S.C. 154(b) by 63 days.

(21) Appl. No.: 15/952,511

(22) Filed: Apr. 13, 2018

(65) Prior Publication Data

US 2018/0230072 A1    Aug. 16, 2018

Related U.S. Application Data

(63) Continuation-in-part of application No. 15/509,764, filed as application No. PCT/US2015/049774 on Sep.
(Continued)

(51) Int. Cl.
*C07C 7/13* (2006.01)
*B01J 20/02* (2006.01)
(Continued)

(52) U.S. Cl.
CPC ............. *C07C 7/13* (2013.01); *B01J 20/0207* (2013.01); *B01J 20/226* (2013.01); *B01J 20/2808* (2013.01); *B01J 20/28033* (2013.01)

(58) Field of Classification Search
None
See application file for complete search history.

(56) References Cited

U.S. PATENT DOCUMENTS

| 4,608,061 A | 1/1986 | Volles et al. |
| 4,773,968 A | 9/1988 | O'Connell et al. |
| | (Continued) | |

FOREIGN PATENT DOCUMENTS

| AU | 2015201045 B2 | 3/2015 |
| EP | 0473828 A1 | 1/1992 |
| | (Continued) | |

OTHER PUBLICATIONS

Silva et al. ("Fixed-Bed Adsorption of n-Pentane/Isopentane Mixtures in Pellets of 5A Zeolite" Ind. Eng. Chem. Res. 1997, 36, 3769-3777) (Year: 1997).*
(Continued)

*Primary Examiner* — Daniel Berns
(74) *Attorney, Agent, or Firm* — Billion & Armitage; Gregory S. Schwartz

(57) ABSTRACT

Embodiments of the present disclosure describe a zeolite-like metal-organic framework composition comprising a metal-organic framework composition with ana topology characterized by the formula $[M^{III}(4, 5\text{-imidazole dicarboxylic acid})_2 X(\text{solvent})_a]_n$, wherein $M^{III}$ comprises a trivalent cation of a rare earth element, X comprises an alkali metal element or alkaline earth metal element, and solvent comprises a guest molecule occupying pores. Embodiments of the present disclosure describe a method of separating paraffins comprising contacting a zeolite-like metal-organic framework with ana topology with a flow of paraffins, and separating the paraffins by size.

19 Claims, 8 Drawing Sheets

Related U.S. Application Data 11, 2015, now Pat. No. 10,486,133, application No. 15/952,511, which is a continuation-in-part of application No. PCT/IB2016/056144, filed on Oct. 13, 2016.

(60) Provisional application No. 62/049,333, filed on Sep. 11, 2014, provisional application No. 62/240,628, filed on Oct. 13, 2015.

(51) Int. Cl.
  *B01J 20/04* (2006.01)
  *B01J 20/22* (2006.01)
  *B01J 20/28* (2006.01)
  *B01J 31/16* (2006.01)

(56) References Cited

U.S. PATENT DOCUMENTS

| | | | |
|---|---|---|---|
| 5,433,770 | A | 7/1995 | Kass et al. |
| 6,318,306 | B1 | 11/2001 | Komatsu |
| 2003/0168024 | A1 | 9/2003 | Qian |
| 2005/0056264 | A1 | 3/2005 | Weissman et al. |
| 2006/0070587 | A1 | 4/2006 | Bhalsora |
| 2006/0144349 | A1 | 7/2006 | Mirji |
| 2006/0287190 | A1* | 12/2006 | Eddaoudi ............. C07F 5/003 502/60 |
| 2007/0202038 | A1 | 8/2007 | Yaghi et al. |
| 2008/0257301 | A1 | 10/2008 | Hotta |
| 2009/0242038 | A1 | 10/2009 | Sengupta et al. |
| 2012/0110984 | A1 | 5/2012 | Shimada et al. |

FOREIGN PATENT DOCUMENTS

| | | |
|---|---|---|
| WO | 2006116340 A1 | 11/2006 |
| WO | 2012175823 A1 | 12/2012 |
| WO | 2014071351 A1 | 5/2014 |
| WO | 2015081237 A1 | 6/2015 |
| WO | 2016048693 A1 | 3/2016 |

OTHER PUBLICATIONS

Huang et al., "Ligand-Directed Strategy for Zeolite-Type Metal—Organic Frameworks: Zinc(II) Imidazolates with Unusual Zeolitic Topologies." Angew. Chem. Int. Ed. (2006), vol. 45, pp. 1557-1559 (published Feb. 20, 2006).*

Notification of Transmittal of the International Search Report and the Written Opinion of the International Searching Authority, or the Declaration for PCT/IB2016/056144 dated Feb. 6, 2017.

Eddaoudi, et al., "Zeolite-Like Metal-Organic Frameworks (ZMOFs): Design, Synthesis, and Properties", Chem. Soc. Rev., vol. 44, Oct. 24, 2014, 228-249.

Phan, et al., "Synthesis, Structure, and Carbon Dioxide Capture Properties of Zeolitic Midazolate Frameworks", Accounts of Chemical Research, vol. 43, No. 1, Oct. 30, 2009, 58-67.

"International Search Report and Written Opinion", International Application No. PCT/US2015/049774, dated Dec. 10, 2015, 10 pages.

Herm, et al., "Separation of Hexane Isomers in a Metal-Organic Framework with Triangular Channels", Science 340, May 24, 2013 960-964.

Nugent, et al., "Porous materials with optimal adsorption thermodynamics and kinetics for CO2 separations", Nature, 495, Mar. 7, 2013, 80-84.

Shekhah, et al., "The liquid phase epitaxy approach for the successful construction of ultra-thin and defect-free ZIF-8 membranes: pure and mixed gas transport study", ChemComm, Royal Society of Chemistry, Feb. 28, 2014, 2089-2092.

Golunski, "what is the point of on-board fuel reforming", Energy Environ. Sci., 2010, 3, 1918-1923.

Jamal, et al., "On-Board Generation of Hydrogen-Rich Gaseous Fuels a Review", Pergamon, Int. J. Hydrogen Energy, 1994, 557-572.

Liu, et al., "Molecular building blocks approach to the assembly of zeolite-like metal—organic frameworks (ZMOFs) with extra-large cavities", The Royal Society of Chemistry, 2006, 1488-1490.

Maythalony, et al., "Quest for Anionic MOF Membranes: Continuous sod-ZMOF Membrane with CO2 Adsorption-Driven Selectivity", J. Am. Chem. Soc. 2015, 137, 1754-1757.

Migliardini, et al., "Adsorption of Light Hydrocarbons on LTA and FER Zeolites", American Journal of Analytical Chemistry, 2013, 4, 109-114.

Peucheret, et al., "Exhaust-gas reforming using precious metal catalysts", Applied Catalysis B: Environmental 65 (2006) 201-206.

Shekhah, et al., "Made-to-order metal-organic frameworks for trace carbon dioxide removal and air capture", Nature Communications, 2014, 7.

Brant, "Toward the Synthesis of Designed Metal-Organic Materials", Thesis. University of South Florida, (c) 2008, pp. 53-56.

* cited by examiner

ZEOLITE-LIKE METAL-ORGANIC FRAMEWORKS WITH ANA TOPOLOGY

BACKGROUND

The oil and gas industries separate linear paraffins from branched paraffins to aid in the production of high quality fuels. For instance, gasoline with a high octane rating results in less engine knocking in internal combustion engines and improved engine performance. Diesel engines, on the other hand, perform optimally with high cetane fuel, which readily ignites under pressures typically observed in a diesel engine. Separating paraffins is important to these industries because the octane rating and cetane rating are directly related to the amount of linear paraffins and branched paraffins present in the fuel. Now that reducing harmful emissions is a matter of global concern, processes that separate linear paraffins from branched paraffins have become increasingly important.

The separation of linear paraffins from branched paraffins, however, remains one of the most intensive and challenging separations of today. Fractionation or distillation processes are employed to separate paraffins, but these processes consume large amounts of energy. Adsorption through zeolite molecular sieves processes are also employed to accomplish the separation, but these processes are less efficient as 3% to 4% of branched paraffins diffuse and/or adsorb on the adsorbent. Metal-organic frameworks offer great potential as an adsorbent or membrane, given the ability to tune or control pore aperture and the potential to alter adsorption and diffusion properties via cation exchange. However, to date, there have been no reports of achieving a complete separation of linear paraffins from branched paraffins using a metal-organic framework.

SUMMARY OF THE INVENTION

In general, this disclosure describes embodiments relating to a zeolite-like metal-organic framework with ana topology. More specifically, this disclosure describes a zeolite-like metal-organic framework with ana topology that may be used to kinetically separate paraffins.

Embodiments of the present disclosure describe a zeolite-like metal-organic framework composition comprising a metal-organic framework composition with ana topology characterized by the formula $[M^{III}(4, 5\text{-imidazole dicarboxylic acid})_2X(\text{solvent})_a]_n$ wherein $M^{III}$ comprises a trivalent cation of a rare earth element, X comprises an alkali metal element or alkaline earth metal element, and solvent comprises a guest molecule occupying pores.

Embodiments of the present disclosure describe a method of separating paraffins comprising contacting a zeolite-like metal-organic framework with ana topology with a flow of paraffins, and separating the paraffins by size.

In one aspect, a method for separating hydrocarbons can include contacting a first component containing a first metal organic framework with a flow of hydrocarbons and separating hydrocarbons by size. In certain embodiments, the hydrocarbons can include alkanes.

In certain embodiments, the method can include separating dibranched hydrocarbons from mono-branched hydrocarbons and linear hydrocarbons. The method can include separating 2,3-dimethylbutane and 2,2-dimethylbutane. The method can include reforming gas using a metal organic framework, other catalysts or steam reforming. The method can include separating hydrocarbons in an automobile.

In certain embodiments, the method can include separating the hydrocarbons into hydrocarbons with low research octane number and hydrocarbons with high research octane number. The method can include moving the hydrocarbons with high research octane number to an internal combustion engine.

In certain embodiments, the internal combustion engine can produce an exhaust gas. In certain embodiments, the method can include reforming the exhaust gas.

In certain embodiments, the reformate can contain hydrogen.

In certain embodiments, the method can include feeding part of the reformate to the internal combustion engine. In certain embodiments, the exhaust gas can be reformed using a metal organic framework, a zeolite catalyst or steam reforming.

The details of one or more examples are set forth in the accompanying drawings and the description below. Other features, objects, and advantages will be apparent from the description and drawings, and from the claims.

BRIEF DESCRIPTION OF THE DRAWINGS

The accompanying drawings illustrate non-limiting example embodiments of the invention.

DETAILED DESCRIPTION

Figure 1:
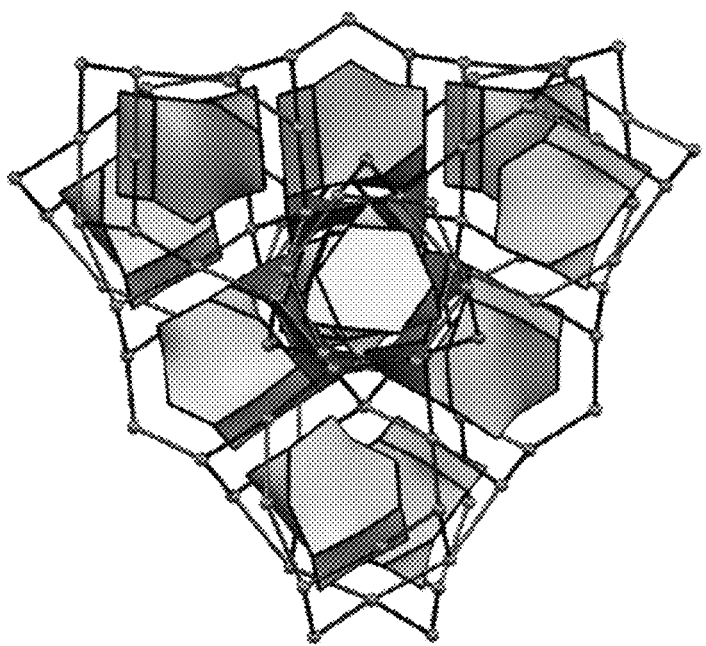
FIG. 1 illustrates a schematic view of a zeolite-like metal-organic framework with ana topology, according to some embodiments.

The present invention relates to a microporous zeolite-like metal-organic framework with ana topology (ana-ZMOF) that can be used as a kinetic-base adsorbent to separate paraffins by size. The disclosure herein provides compositions of ana-ZMOF and methods of separating paraffins using an ana-ZMOF. The ana-ZMOF described herein can be used as a kinetic-based adsorbent to about completely separate paraffins by size. The ana-ZMOF can be fabricated as a molecular sieve or as a thin-film membrane. The adsorption and diffusion properties of ana-ZMOF, which is anionic, can be altered or modified through cation exchange. The pore aperture sizes of the ana-ZMOF disclosed herein can be tuned to within a difference of less than about 0.5 Angstroms (Å). Embodiments provided herein describe a chemical formula of an ana-ZMOF. Embodiments further describe a method of separating paraffins by size using an ana-ZMOF. Embodiments further describe an ana-ZMOF used as a kinetics-based adsorbent for kinetic sieving of linear paraffins from branched paraffins involving molecules with a kinetics diameter of greater than about 4.2 Å. Embodiments provided herein describe employing ana-ZMOF as an adsorbent to achieve a full sieving of di-branched paraffins and tri-branched paraffins. Embodiments provided herein describe employing ana-ZMOF as an adsorbent to separate pentane from iso-pentane. Embodiments provided herein also describe employing ana-ZMOF as an adsorbent to achieve about a full sieving of 2,2,4-trimethylpenthane. Embodiments describe employing ana-ZMOF as a molecular sieve to separate high octane rating paraffins from low octane rating mono-branched paraffins and linear paraffins with infinite selectivity. Numerous other advantages and uses of an ana-ZMOF will be readily apparent to one of skill in the art.

The figures referenced in the description of the many embodiments of this disclosure are not necessarily drawn to scale and they are provided merely to illustrate the invention. Several aspects of the invention are described below with reference to example applications for illustration. It should be understood that numerous specific details, relationships, and methods are set forth to provide an understanding of the invention. One skilled in the relevant art, however, will readily recognize that the invention can be practiced without one or more of the specific details or with other methods. In other instances, well-known structures or operations are not shown in detail to avoid obscuring the invention. The present invention is not limited by the illustrated ordering of acts or events, as some acts may occur in different orders and/or concurrently with other acts or events. Furthermore, not all illustrated acts or events are required to implement a methodology in accordance with the present invention.

Many terms used herein are defined below. Other terms not expressly defined should be read in the context of this specification before being given their ordinary meanings as understood by one of skill in the art.

As used herein, "rare earth element" refers to cerium, dysprosium, erbium, europium, gadolinium, holmium, lanthanum, lutetium, neodymium, praseodymium, promethium, samarium, scandium, terbium, thulium, ytterbium, or yttrium.

As used herein, "alkali metal element" refers to lithium, sodium, potassium, rubidium, caesium, or francium.

As used herein, "alkaline earth metal element" refers to beryllium, magnesium, calcium, strontium, barium, or radium.

As used herein, "paraffin" refers to $C_nH_{2n+2}$, wherein n- as a prefix refers to a linear paraffin and iso- as a prefix refers to a branched paraffin.

Zeolites are purely inorganic crystalline microporous materials of commercial significance. A defining feature of zeolites is a three-dimensional framework comprised of Si and/or Al tetrahedral metal ions linked by oxide ions at a pre-defined angle. These tetrahedra link to form a variety of structures with regular intra-crystalline cavities and channels of molecular dimensions, and bear a net negative charge that is balanced by an extra-framework cation. As a size-selective adsorbent, zeolites are employed as molecule sieves or membranes to achieve separations through a difference in molecular diameter and pore aperture, where molecules with a diameter less than the pore aperture diameter adsorb and/or diffuse through the adsorbent, leaving any molecules with diameters greater than the pore diameter in the bulk phase.

Zeolites have been particularly effective as molecular sieves to separate linear hydrocarbons, such as n-butane and n-pentane, from branched hydrocarbons, such as iso-butane and iso-pentane. The ongoing challenge with zeolites, however, is the inability to tune pore size with greater precision to achieve more efficient separations. For instance, Zeolite 5 Å, with a pore aperture of 4.2 Å, does not achieve a full sieving of linear paraffins, as about 3% to 4% of the valuable branched paraffins are lost due to diffusion and adsorption on the adsorbent. Despite the maturity of zeolite chemistry, zeolite technology has not allowed tuning of pore size in the range lower than 1 Å difference in pore aperture size. For example, existing zeolite molecular sieves are characterized as 3 Å, 4 Å, and 5 Å.

Metal-organic frameworks (MOF), on the other hand, have exhibited much more control over pore size than zeolites. For instance, MOFs exhibit control of pore size to within a range of less than 0.5 Å in difference. A MOF is a crystalline material that combines ligands and metal ions or metal clusters to form one-, two-, and three-dimensional networked structures with large surface areas that can be porous. While the tunable pore size, structure, functionality, and properties of MOFs make them attractive for a variety of applications, including, among other things, gas separations, only a few examples of MOFs exhibiting kinetic-based gas separations have been reported. Moreover, almost no examples of using MOFs to achieve a full sieving in gas separations at 298K have been reported.

Metal-organic frameworks with zeolite-like topologies, or ZMOFs, have shown great promise for kinetic-based and gas sieving separation processes in bulk adsorbent and membrane forms. The topologies of ZMOFs are isomorphic with zeolites. ZMOFs exhibit properties such as tunable pore sizes and cavities, chemical stability, and the ability to control and tune extra-framework cations via ion exchange. ZMOFs are constructed from a single-metal-ion-based molecular building block (MBB) that can be produced in situ from single metal ions heterochelated by multifunctional ligands. ZMOFs have been described, for example, in U.S. Pat. No. 8,415,493, which is hereby incorporated by reference in its entirety.

The present invention relates to a zeolite-like metal-organic framework with ana topology (ana-ZMOF) and its use as a material for separating paraffins. See FIG. 1, for example, which is a schematic view of a zeolite-like metal-organic framework with ana topology, according to some embodiments.

The composition of the ana-ZMOF is characterized by the formula $[M^{III}(4,5\text{-imidazole dicarboxylic acid})_2 X (\text{solvent})_a]_n$, wherein n represents the number of molecular building blocks.

In some embodiments, $M^{III}$ comprises one or more of a trivalent cation of a rare earth element, including cerium ($Ce^{3+}$), dysprosium ($Dy^{3+}$), erbium ($Er^{3+}$), europium ($Eu^{3+}$), gadolinium ($Gd^{3+}$), holmium ($Ho^{3+}$), lanthanum ($La^{3+}$), lutetium ($Lu^{3+}$), neodymium ($Nd^{3+}$), praseodymium ($Pr^{3+}$), promethium ($Pm^{3+}$), samarium ($Sm^{3+}$), scandium ($Sc^{3+}$), terbium ($Tb^{3+}$), thulium ($Tm^{3+}$), ytterbium ($Yb^{3+}$), or yttrium ($Y^{3+}$).

In some embodiments, the ligand is a heterofunctional ditopic ligand, such as 4,5-imidazole dicarboxylic acid (ImDC). ImDC possesses two N- and O-hetero-chelating moieties with a potential angle of 144°, as directed by the metal-nitrogen coordination. In some embodiments the ligand is one or more of 1H-Imidazole-2-carboxylic acid, pyrimidine-4,6-dicarboxcylic acid, and pyridine-2,5-dicarboxylic acid. Different properties may be observed with slight variations in the bulky character of a ligand and in a ligand's size (e.g., length).

In some embodiments, X comprises one or more of an alkali metal element, including lithium, sodium, potassium, rubidium, cesium, or francium. In other embodiments, X comprises one or more of an alkaline earth metal element, including beryllium, magnesium, calcium, strontium, barium, or radium.

A solvent comprises a guest molecule that, as a result of synthesis, occupies pores of the ana-ZMOF. In some embodiments, the solvent can be $H_2O$, N,N-dimethyl formamide (DMF), ethanol, 4,4;-trimethylene-dipiperidine, or 1,2-diaminocyclohexane. In other embodiments, the solvent guest molecules are evacuated. Consequently, a can vary down to zero, without any change in the definitional framework of the ana-ZMOF.

An ana topology is characterized by a $M^{III}$ cation connected to four organic linkers in a tetrahedral arrangement. These tetrahedral units connect to form four- and six-membered rings that delimit a three-dimensional channel system with distorted eight-membered ring openings.

The ana-ZMOF disclosed herein can be used to separate paraffins. In some embodiments, the ana-ZMOF may be used to separate paraffins by size. In other embodiments, the ana-ZMOF may be used to separate paraffins based on a degree of branching. In some embodiments, the ana-ZMOF may be used to separate isoparaffins from paraffins. In other embodiments, the ana-ZMOF may be used to separate linear paraffins from branched paraffins. Single component adsorption isotherms of linear paraffins and branched paraffins illustrate that the adsorption of linear paraffins is nearly double the adsorption of branched paraffins. In addition, an analysis of the kinetics of sorption on ana-ZMOF shows that linear paraffins are adsorbed at a much faster rate than branched paraffins. Consequently, ana-ZMOF is the ideal candidate material for kinetically separating linear paraffins from branched paraffins.

In some embodiments, the separation is kinetically driven. For example, in some embodiments, the separation of linear paraffins from branched paraffins is kinetic-based, as opposed to equilibrium-based. In some embodiments, the separation is based on a difference in kinetic diameter and pore aperture size, wherein paraffins with a kinetic diameter that is less than the pore aperture diameter diffuse and/or adsorb on the ana-ZMOF and paraffins with a kinetic diameter that is greater than the pore aperture diameter remain in the bulk phase. In some embodiments, ana-ZMOF is used to separate paraffins with a kinetics diameter greater than about 4.2 Å to about 5 Å. In some embodiments, the separation is based on a difference in time that it takes a paraffin to reach equilibrium for sorption on an ana-ZMOF, wherein the time it takes a branched paraffin to reach equilibrium is much greater than the time it takes a linear paraffin to do the same. In some embodiments, the separation is based on both a difference in kinetic diameter and/or pore size, and a difference in equilibrium times.

A method of separating paraffins comprises contacting a zeolite-like metal-organic framework with ana topology with a flow of paraffins, and kinetically and completely separating paraffins by size and/or based on a degree of branching. In some embodiments, ana-ZMOF is used to separate isoparaffins from paraffins. In some embodiments, ana-ZMOF is used to separate linear paraffins from branched paraffins. In some embodiments, ana-ZMOF is used to separate linear paraffins from mono-branched paraffins, di-branched paraffins, tri-branched paraffins, cyclic paraffins, and other more highly branched paraffins. In some embodiments, ana-ZMOF is used to separate one or more of linear paraffins and mono-branched paraffins from one or more of di-branched paraffins, tri-branched paraffins, cyclic paraffins, and other more highly branched paraffins. In some embodiments, ana-ZMOF is used to separate paraffins with a high octane rating from paraffins with a low octane rating. In some embodiments, ana-ZMOF is used to separate paraffins with a high cetane rating from paraffins with a low cetane rating.

In some embodiments, ana-ZMOF is used as a kinetic-based adsorbent to separate linear paraffins from branched paraffins, wherein the separation involves molecules with a kinetics diameter of greater than about 4.2 Å to about 5 Å.

In some embodiments, ana-ZMOF is used to achieve a full sieving or a complete separation of linear paraffins from branched paraffins, resulting in an efficient separation of paraffins. In some embodiments, ana-ZMOF achieves a full sieving of di-branched paraffins. In some embodiments, ana-ZMOF achieves a full sieving of tri-branched paraffins.

Figure 2:
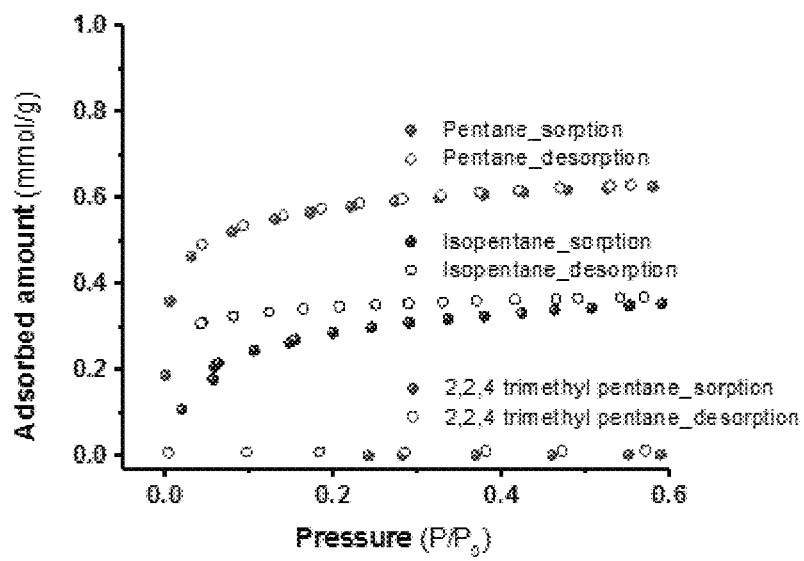
FIG. 2 illustrates a graphical view of single-component adsorption isotherms for pentane, isopentane, and 2,2,4-trimethylpentane on a zeolite-like metal-organic framework with ana topology, indicating the amount of pentane, isopentane, and 2,2,4-trimethylpentane adsorbed with changes in pressure at 20° C., according to some embodiments.

The ana-ZMOF can be used as a kinetic-based adsorbent to kinetically separate pentane from isopentane. FIG. 2 illustrates a graphical view of single-component adsorption isotherms for pentane, isopentane, and 2,2,4-trimethylpentane on a zeolite-like metal-organic framework with ana topology, indicating the amount of pentane, isopentane, and 2,2,4-trimethylpentane adsorbed with changes in pressure at 20° C. With respect to the separation of n-pentane from isopentane, FIG. 2 illustrates that the adsorption of pentane on an ana-ZMOF is almost double the adsorption of isopentane. With respect to 2,2,4-trimethylpentane, FIG. 2 illustrates that 2,2,4-trimethypentane was experimentally not observed adsorbing onto or diffusing into the pores of ana-ZMOF. In some embodiments, ana-ZMOF can be used as a molecular sieve to separate high octane rating gasoline components from low octane rating gasoline components comprising mono-branched paraffins and linear paraffins, with infinite selectivity.

Figure 3:
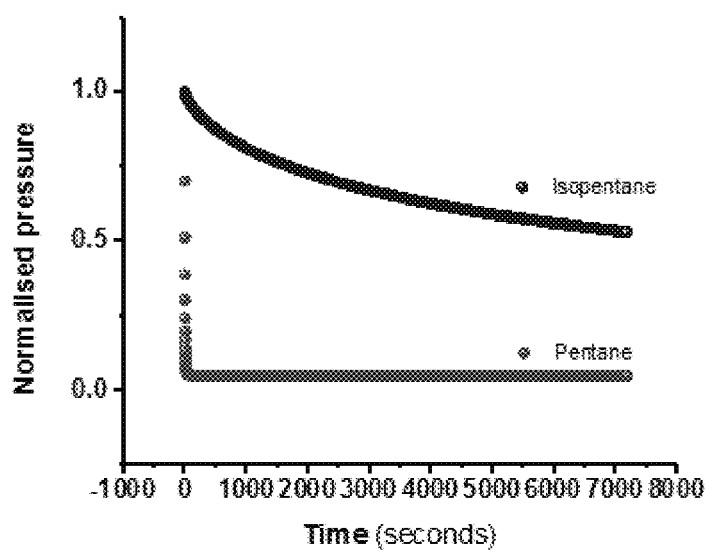
FIG. 3 illustrates a graphical view of the adsorption of pentane and isopentane on a zeolite-like metal-organic framework with ana topology, indicating the normalized pressure of pentane and isopentane as a function of time at 20° C., according to some embodiments.

FIG. 3 illustrates a graphical view of the adsorption of pentane and isopentane on a zeolite-like metal-organic framework with ana topology, indicating the normalized pressure of pentane and isopentane as a function of time at 20° C. More specifically, FIG. 3 illustrates that an analysis of the kinetics of sorption clearly show that pentane is adsorbed much faster than isopentane, with a time of greater than 5000 seconds for the sorption of isopentane to reach equilibrium.

The ana-ZMOF disclosed herein is anionic. The adsorption and/or diffusion properties of an ana-ZMOF can be altered and/or modified through cation exchange. In some embodiments, the pore size or pore aperture of an ana-ZMOF is tuned via cation exchange. In some embodiments, pore size is tuned through cation exchange with an alkali metal ion or alkaline earth metal ion. In some embodiments, the pore size of an ana-ZMOF is tuned to within a range that is less than about 1 Å in difference. In some embodiments, the pore size of an ana-ZMOF is tuned to about 4.2 Å to 5 Å. In some embodiments, the pore size of an ana-ZMOF is tuned to within a range of less than about 0.5 Å in difference.

The ana-ZMOF disclosed herein can be used as a molecular sieve adsorbent or as a thin-film membrane. In some embodiments, ana-ZMOF is used as a molecular sieve adsorbent to separate linear paraffins from branched paraffins. In some embodiments, ana-ZMOF is used as a thin-film membrane to separate linear paraffins from branched paraffins. In some embodiments, a thin-film membrane comprising ana-ZMOF is fabricated on a support, such as a porous ceramic substrate. In some embodiments, a thin-film membrane comprising ana-ZMOF is fabricated on an alumina substrate.

Figure 4:
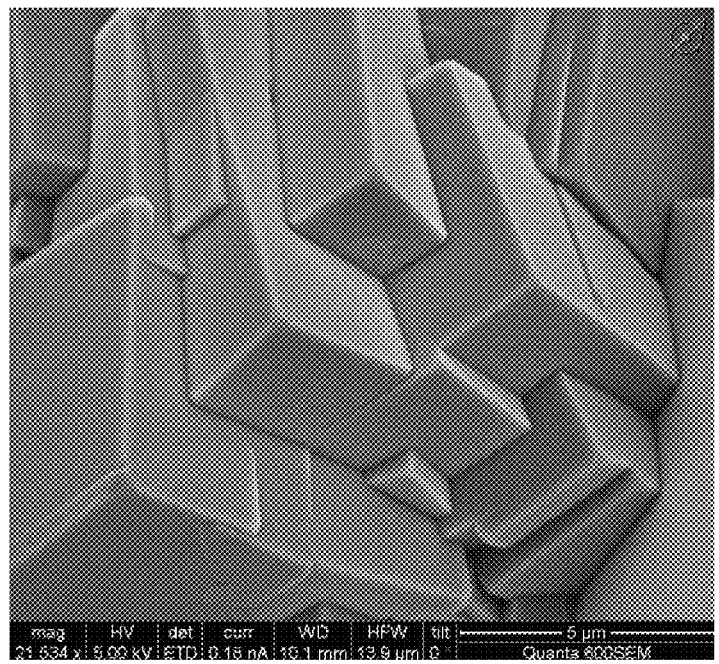
FIG. 4 illustrates a scanning electron microscopy image with a view from the top of a zeolite-like metal-organic framework with ana topology membrane fabricated on alumina substrate, according to some embodiments.
Figure 5:
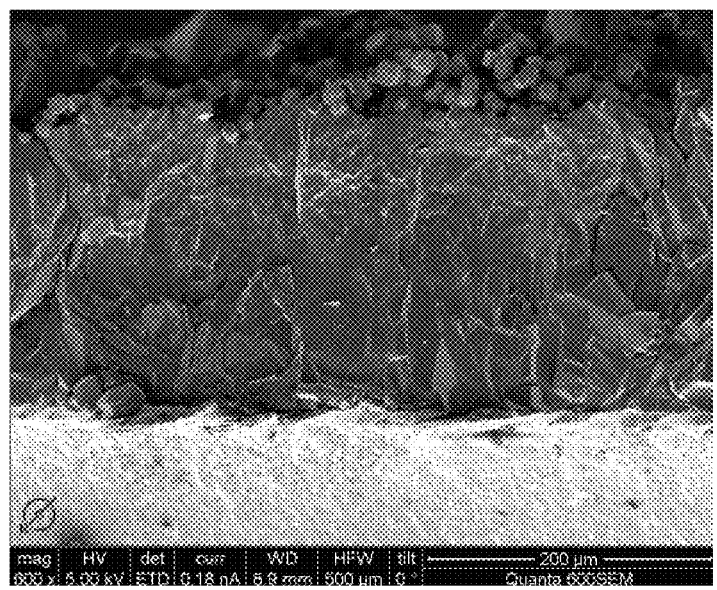
FIG. 5 illustrates a scanning electron microscopy image with a view of the cross-section of a zeolite-like metal-organic framework with ana topology membrane fabricated on alumina substrate, according to some embodiments.

An ana-ZMOF pure membrane was fabricated and fully characterized. The continuity of the membrane was tested by the separation of gas mixtures like $CO_2/H_2$ and $CO_2/CH_4$. Pursuant to these tests, ana-ZMOF showed a selectivity for $CO_2$ of 2.5 and 4, respectively. FIG. 4 illustrates a scanning electron microscopy image with a view from the top of a zeolite-like metal-organic framework with ana topology membrane fabricated on alumina substrate. FIG. 5 illustrates a scanning electron microscopy image with a view of the cross-section of a zeolite-like metal-organic framework with ana topology membrane fabricated on alumina substrate.

The use of ana-ZMOF to separate valuable highly branched paraffins from less valuable linear paraffins to enrich fuel is economically significant. Branched paraffins generally observe a higher octane rating than linear paraffins. This is particularly important in internal combustion engines, as high octane rating fuel results in less engine knocking and improved engine performance. On the other hand, diesel engines perform optimally with high cetane fuel because it readily ignites under pressures typically observed in a diesel engine. For diesel engines, linear paraffins are assigned a higher cetane rating number. Consequently, with respect to diesel fuel, linear paraffins are more valuable than branched paraffins. The ana-ZMOF's ability to completely separate linear paraffins from branched paraffins, together with its high chemical stability, make it an ideal candidate as a kinetic-based adsorbent for fuel enrichment.

Figure 6:
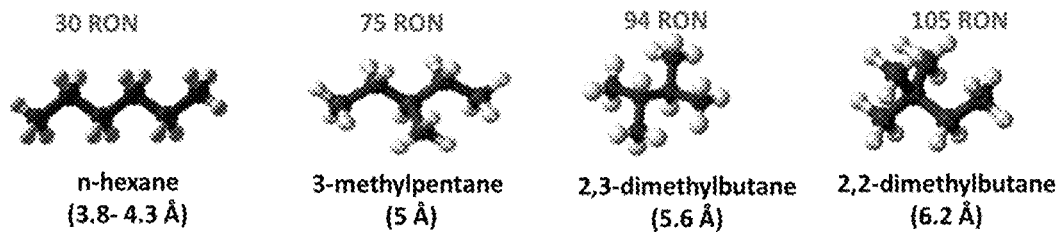
FIG. 6 illustrates a representation of gasoline through a schematic view of isomers of hexane with their corresponding kinetic diameters and Research Octane Numbers (RON), according to some embodiments.
Figure 7:
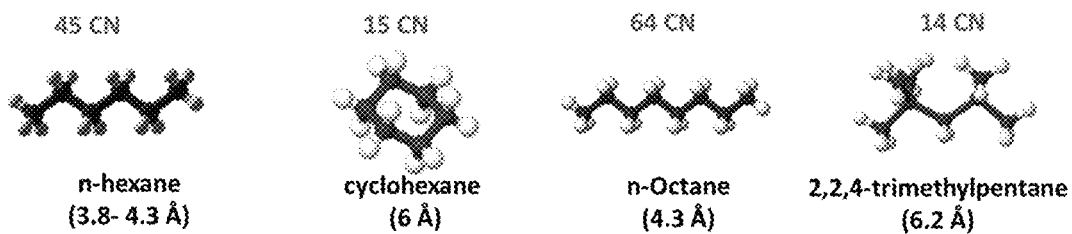
FIG. 7 illustrates a representation of the components of diesel fuel through a schematic view of paraffins with their corresponding kinetic diameters and Research Octane Numbers (RON), according to some embodiments.

FIG. 6 illustrates a representation of gasoline through a schematic view of isomers of hexane with their corresponding kinetic diameters and Research Octane Numbers (RON). Given the unique properties of ana-ZMOF, ana-ZMOF can kinetically separate n-hexane from its larger, higher RON isomers, such as 3-methylpentane, 2,3-dimethtylbutane, and 2,2-dimethylbutane. FIG. 7 illustrates a representation of the components of diesel fuel through a schematic view of paraffins with their corresponding kinetic diameters and Research Octane Numbers. Similarly, ana-ZMOF can kinetically separate n-hexane and n-octane from lower centane number paraffins with larger kinetic diameters, such as cyclohexane and 2,2,4-trimethylpentane. ana-ZMOF's ability to separate other valuable paraffins will be readily apparent to one of skill in the art.

Methods and systems are described herein for separating fuel streams via one or more MOFs for use in optimizing internal combustion engine (ICE) fuels, such as diesel and gasoline, and providing feed streams for fuel reformers. MOFs can separate fuel streams using various methods. The practicality of the adsorptive separation technology and its associated efficiency are strongly dependent and directly correlated to the intrinsic properties of the employed separation adsorbent. Adsorptive separation can be accomplished by one of three mechanisms: steric, kinetic, or equilibrium-based. The steric effect originates from molecular sieving properties of the adsorbent, wherein only relatively small and appropriately shaped molecules can diffuse into the adsorbent while the other molecules are totally excluded. In contrast, kinetic adsorption is based on the differences in diffusion rates of different adsorbate molecules.

Metal organic frameworks (MOFs) are a versatile and promising class of crystalline solid state materials which MOFs are architecturally robust and can have a porosity of greater than 50% of the MOF crystal volume. The surface area values of such MOFs can range from 200 to 7,000 $m^2/g$, thus exceeding those of traditional porous materials such as zeolites and carbons. The ordered crystalline structures of MOFs allow porosity and functionality (e.g., permeselectivity toward mono-branched and n-paraffins), to be tailored towards various applications while retaining isoreticular topologies. For example, MOFs with large pore apertures and low densities can be tailored for selective inclusion of large molecules and proteins, both as a storage means and/or as a reaction facilitation platform. MOFs can exhibit porosity through a configuration of one or more of channels and cages throughout the networked architecture.

Further, the thermal and chemical stability of many MOFs has made them amenable to post-synthetic covalent organic and metal-complex functionalization. These capabilities enable substantial enhancement of gas storage in MOFs and have led to their extensive study in the catalysis of organic reactions, activation of small molecules (hydrogen, methane, and water), hydrocarbon and gas separation, and fuel storage.

Generally, MOFs comprise a network of nodes and ligands, wherein a node has a connectivity capability at two or more functional sites, and a ligand has a connectivity capability at least at two functional sites, each of which connect to a node. Nodes are typically metal ions or metal containing clusters. Ligands are typically poly-functional, or polytopic, organic molecules, and comprise two or more functional sites capable of each connecting to a node. In some instances, ligands with node connectivity capability at two or more functional sites can also be characterized as nodes. Ligands can include two functional sites capable of each connecting to a node, and optionally one or more additional functional sites which do not connect to nodes within a particular framework. In some embodiments, polytopic ligands can be heteropolytopic, wherein at least one of the two or more functional sites differs from another functional site.

A MOF can comprise a metal-based node and an organic ligand which extrapolate to form a coordination network. Such coordination networks have advantageous crystalline and porous characteristics affecting structural integrity and interaction with foreign species (e.g., hydrocarbons). The particular combination of nodes and ligands within a framework will dictate the framework topology and functionality. Through ligand modification or functionalization, the environment in the internal pores can be modified to suit specific applications.

MOF can be represented by the formula [(node)$_a$(ligand)$_b$(solvent)$_c$]$_n$, wherein n represents the number of molecular building blocks. Solvent represents a guest molecule occupying pores within the MOF, for example as a result of MOF synthesis, and can be evacuated after synthesis to provide a MOF with unoccupied pores. Accordingly, the value of c can vary down to zero, without changing the definitional framework of the MOF. Therefore, in many instances, MOFs can be defined as [(node)$_a$(ligand)$_b$]$_n$, without reference to a solvent or guest molecule component.

Disclosed herein are systems and methods utilizing MOFs for upgrading ICE fuel, and optimizing ICE performance MOFs suitable for the methods described herein can be chosen based on the pore aperture size of the MOF. The pore aperture size refers to the size of the aperture which gives access to a cage. In case of channels, the average pore diameter can be the same as the aperture size. MOFs suitable for the methods described herein can be chosen based on the average pore size of the MOF. An average pore size refers to the size of one or more of the channels and cages present within a MOF architecture. For example, a key parameter that drives the separation of aliphatic unbranched paraffins (i.e., n-paraffins) from branched paraffins (i.e., iso-paraffins) is the aperture size of an MOF.

Gasoline Upgrading

Disclosed herein are systems and methods for optimizing the performance of an ICE by altering the Research Octane Number (RON) value of fuel. RON is a rating assigned to individual fuel constituents based on the performance of an engine fueled by a particular fuel constituent. The weighted average of RON values for all individual fuel constituents indicate the RON value of a fuel. RON values is determined by running the fuel in a test engine with a variable compression ratio under controlled conditions, and comparing the results with those for mixtures of iso-octane and n-heptane. Generally, the magnitude of the RON value relates to the amount of compression a fuel constituent can withstand before igniting. Fuels with higher RON values increase the performance of non-compression ICEs (i.e., gasoline ICEs), as fuel can be more highly compressed before being ignited. Gasoline with lower RON numbers can lead to engine knocking, which is detrimental to performance and engine longevity.

A higher degree of branching can increase the RON value of a paraffin isomer. As used herein, "paraffin" refers to alkanes, or saturated hydrocarbons molecules consisting of hydrogen and carbon atoms connected by single bonds. Paraffins can include aliphatic (i.e., open chain) and cyclic alkanes. For example, an unbranched alkane such as n-hexane:

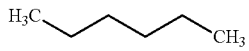

with a kinetic diameter of 3.8-4.3 Å, has a RON value of 30. Monobranched alkane 2-methylpentane:

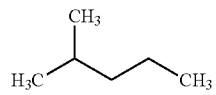

has a RON value of 75, and monobranched alkane 3-methylpentane:

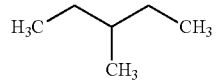

with a kinetic diameter of 5 Å, has a RON value of 75. Similarly, dibranched alkane 2,3-dimethylbutane:

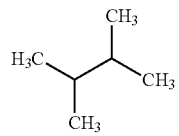

with a kinetic diameter of 5.6 Å, has a RON value of 94, and dibranched alkane 2,2-dimethylbutane:

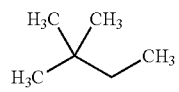

with a kinetic diameter of 6.2 Å, has a RON value of 105. Accordingly, the dibranched paraffin isomers, such as hexanes, are more valuable gasoline constituents than monobranched paraffin isomers and unbranched paraffin isomers.

Figure 8:
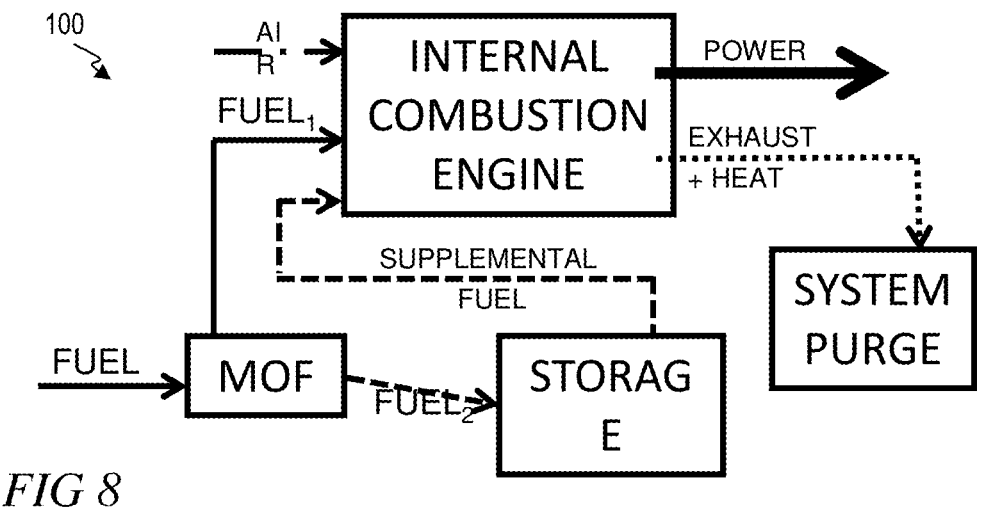
FIG. 8 illustrates a schematic view of a system and method for optimizing an internal combustion engine, according to one or more embodiments.

The systems and methods provided herein can optimize the performance of a gasoline ICE by isolating dibranched paraffins from mono-branched and n-paraffins to alter the RON value of fuel injected into the ICE. FIG. 8 illustrates a system and method 100 for optimizing an ICE by separating a fuel into two or more streams. System and method 100 can be performed on-board a vehicle. System and method 100 comprises contacting a fuel with an MOF, and separating the fuel into a first fuel stream (Fuels) and a second fuel stream (Fuel$_2$). Fuel can be supplied by a fuel source, such as a fuel tank. Fuel can contact the MOF in a liquid state, a gaseous state, or combinations thereof.

Suitable MOFs will be described below. In some embodiments, separating occurs by the MOF selectively sorbing one or more constituents of the fuel, and subsequently desorbing the selectively sorbed one or more constituents to form a first fuel stream or a second fuel stream. Sorption can include one or more of adsorption and desorption. In some embodiments, separating occurs by the MOF structure, in the form of a membrane or packed bed or column, selectively allowing one or more fuel constituents to permeate the MOF structure. An MOF has "permeselectivity" for a constituent which is selectively permitted to permeate the MOF structure. Suitable MOFs generally have very rigid structures, which are capable of maintaining structural stability over a number of sorption/desorption cycles, and/or over a high volume of constituent permeation. In some embodiments, suitable MOFs will have aperture sizes between about 0.4 nm and about 0.6 nm, between about 0.45 and about 0.55 nm, or between about 0.4 and 0.5 nm. The MOF can separate the fuel based on the degree of branching of the fuel constituent isomers. Accordingly, the MOF can separate the fuel based on RON value. MOFs can separate fuel constituent isomers of butanes, pentanes, hexanes, heptanes, octanes, nonanes and decanes. In one embodiment, the first fuel stream has a higher RON value than the second fuel stream. In one embodiment, the second fuel stream has a higher RON value than the first fuel stream.

The first fuel stream can then be injected into an ICE in combination with air, wherein the first fuel stream is combusted, generating power, heat, and exhaust. The major components (i.e., those comprising greater than about 1%) of exhaust from a vehicle with an ICE typically include $N_2$, $CO_2$, CO, $H_2O$, and $O_2$. Minor components (i.e., those comprising less than about 1%) of ICE exhaust typically include $SO_x$ compounds (e.g., $SO_2$, $SO_3$), $NO_x$ compounds (e.g., NO, $NO_2$), low molecular weight aldehydes (e.g., HCHO), low molecular weight organic acids (e.g., HCOOH), low molecular weight alcohols (e.g., $CH_3OH$), and hydrocarbons (e.g., $C_nH_m$). For spark ignition (i.e., gasoline) ICEs, $H_2$ and CO typically comprise major components of exhaust. For compression ignition (i.e., diesel) ICEs, $H_2$ and CO typically comprise minor components of exhaust. In a vehicle utilizing oxy-combustion capture, the nitrogen is substantially removed from air to create an oxygen input stream. The exhaust from this type of vehicle typically contains significantly higher amounts of $CO_2$ and $H_2O$ by weight, and very small amounts of $N_2$. Air can comprise ambient air, or a mixture of one or more of oxygen, nitrogen, and carbon dioxide. Heat and exhaust can be directed to a system purge. System purge can comprise an exhaust to atmosphere. System purge can comprise a storage vessel. For example, a storage vessel can collect one or more of $H_2$ or $CO_2$. System purge can comprise a combination of exhaust to atmosphere and a storage vessel. The second fuel stream can be directed to storage. Fuel in storage can optionally be injected into the ICE as a supplemental fuel stream.

In one embodiment, the first fuel stream has a higher RON value than the second fuel stream, and is injected into the ICE to increase performance. The second fuel stream can be stored for subsequent discharge or removal. Alternatively or additionally, the second fuel stream can be injected into the ICE as supplemental fuel when high performance is not required or desired. For example, system and method 100 can selectively direct dibranched paraffin isomers into the first fuel stream to increase engine performance, and selectively direct monobranched and unbranched paraffin isomers into the second fuel stream. In a specific embodiment, system and method 100 can selectively direct 2,3-dimethylbutane and 2,2-dimethylbutane into the first fuel stream to increase engine performance, and selectively direct monobranched hexane isomers and n-hexane into the second fuel stream. In this specific embodiment, an MOF based membrane with high permselectivity toward mono-branched and n-paraffins vs. di-branched paraffins, can be used.

In one embodiment, the first fuel stream has a lower RON value than the second fuel stream, and is injected into the ICE to provide a threshold level of performance. The second fuel stream can be stored for subsequent discharge or removal. Alternatively or additionally, the second fuel stream can be injected into the ICE as supplemental fuel when higher performance is required or desired. For example, system and method 100 can selectively direct monobranched and unbranched paraffin isomers into the first fuel stream to provide a threshold level of performance, and selectively direct dibranched paraffin isomers into the second fuel stream. In a specific embodiment, system and method 100 can selectively direct monobranched hexane isomers and n-hexane into the first fuel stream to provide a threshold level of performance, and selectively direct 2,3-dimethylbutane and 2,2-dimethylbutane into the second fuel stream. In this specific embodiment, an MOF based membrane with high permselectivity toward mono-branched and n-paraffins vs. di-branched paraffins, can be used.

Diesel Upgrading

Disclosed herein are systems and methods for optimizing the performance of a diesel ICE by altering the Cetane Number (CN) value of fuel. A CN value is similar to a RON value, but is applied to diesel fuels and is a measurement of the combustion during compression ignition. The CN value is used to measure the quality of this combustion according to the self-ignition delay. A higher CN value indicates a shorter self-ignition delay of a fuel more complete combustion of fuel. As fuel burns faster and more completely in a diesel ICE, the engine experiences greater performance and produces fewer harmful emissions. Conversely, fuels with low CN values are slower to ignite and do not burn completely.

Generally, unbranched aliphatic paraffins have higher CN values than branched or cyclic isomers. For example, an unbranched alkane such as n-hexane:

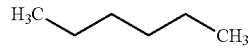

with a kinetic diameter of 3.8-4.3 Å, has a CN value of 45, while a cyclic cyclohexane isomer:

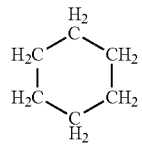

with a kinetic diameter of 6 Å, has a CN value of 15. Similarly, an unbranched alkane such as n-octane:

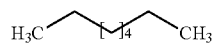

with a kinetic diameter of 4.3 Å, has a CN value of 64, while a branched 2,2,4-trimethylpentane isomer:

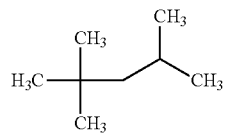

with a kinetic diameter of 6.2 Å, has a CN value of 14. Accordingly, the unbranched aliphatic paraffin isomers, such as n-hexane, are more valuable diesel fuel constituents than branched and cyclic paraffin isomers. Further, Cn paraffins have higher CN values than Cn olefins. As used herein, "olefin" refers to alkenes, or unsaturated hydrocarbons molecules consisting of hydrogen and carbon atoms with at least one carbon-to-carbon double bond. Oleffins can include aliphatic (i.e., open chain) and cyclic alkenes.

The systems and methods provided herein can optimize the performance of a diesel ICE by isolating unbranched aliphatic paraffin isomers from branched and cyclic paraffin isomers to alter the CN value of fuel injected into the ICE. System and method 100, as illustrated in FIG. 8, can also optimize a diesel ICE. System and method 100 comprises contacting a fuel with an MOF, and separating the fuel into a first fuel stream ($Fuel_1$) and a second fuel stream ($Fuel_2$). Fuel can be supplied by a fuel source, such as a fuel tank. Fuel can contact the MOF in a liquid state, a gaseous state, or combinations thereof.

Suitable MOFs will be described below. Suitable MOFs generally have very rigid structures, which are capable of maintaining structural stability over a number of sorption/desorption cycles. Separating occurs by the MOF selectively sorbing one or more constituents of the fuel, and subsequently desorbing the selectively sorbed one or more constituents to form a first fuel stream or a second fuel stream. Sorption can include one or more of adsorption and desorption. In some embodiments, separating occurs by the MOF structure, in the form of a membrane or packed bed or column, selectively allowing one or more fuel constituents to permeate the MOF structure. Suitable MOFs generally have very rigid structures, which are capable of maintaining structural stability over a number of sorption/desorption cycles, and/or over a high volume of constituent permeation. In some embodiments, suitable MOFs will have aperture sizes between about 0.4 nm and about 0.6 nm, between about 0.45 and about 0.55 nm, or between about 0.4 and 0.5 nm. The MOF can separate the fuel based on the degree of branching and cyclic/aliphatic molecular construction of the fuel constituent isomers. Accordingly, the MOF can separate the fuel based on CN value. MOFs can separate fuel constituent isomers of butanes, pentanes, hexanes, heptanes, octanes, nonanes and decanes. In one embodiment, the first fuel stream has a higher CN value than the second fuel stream. In one embodiment, the second fuel stream has a higher CN value than the first fuel stream.

The first fuel stream can then be injected into an ICE in combination with air, wherein the first fuel stream is combusted, generating power, heat, and exhaust. Air can comprise ambient air, or a mixture of one or more of oxygen, nitrogen, and carbon dioxide. Heat and exhaust can be directed to a system purge. System purge can comprise an exhaust to atmosphere. System purge can comprise a storage vessel. For example, a storage vessel can collect one or more of $H_2$ or $CO_2$. System purge can comprise a combination of exhaust to atmosphere and a storage vessel. The second fuel stream can be directed to storage. Fuel in storage can optionally be injected into the ICE as a supplemental fuel stream.

In one embodiment, the first fuel stream has a higher CN value than the second fuel stream, and is injected into the ICE to increase performance. The second fuel stream can be stored for subsequent discharge or removal. Alternatively or additionally, the second fuel stream can be injected into the ICE as supplemental fuel when high performance is not required or desired. For example, system and method 100 can selectively direct unbranched aliphatic paraffin isomers into the first fuel stream to increase engine performance, and selectively direct oleffins and branched and cyclic paraffin isomers into the second fuel stream. Aromatic compounds and polynuclear aromatic compounds can optionally be directed into the second fuel stream. In a specific embodiment, system and method 100 can selectively direct aliphatic $C_7$-$C_{20}$ n-paraffins into the first fuel stream to increase engine performance, and selectively direct cyclohexane and branched octane isomers into the second fuel stream. In this specific embodiment, an MOF based membrane with high permeselectivity toward unbranched aliphatic paraffins vs. branched and cyclic paraffins, can be used.

In one embodiment, the first fuel stream has a lower CN value than the second fuel stream, and is injected into the ICE to provide a threshold level of performance. The second fuel stream can be stored for subsequent discharge or removal. Alternatively or additionally, the second fuel stream can be injected into the ICE as supplemental fuel when higher performance is required or desired. For example, system and method 100 can selectively direct branched and cyclic paraffin isomers into the first fuel stream to provide a threshold level of performance, and selectively direct unbranched aliphatic paraffin isomers into the second fuel stream. In a specific embodiment, system and method 100 can selectively direct cyclohexane and branched octane isomers into the first fuel stream to provide a threshold level of performance, and selectively direct n-hexane and n-octane into the second fuel stream. In this specific embodiment, an MOF based membrane with high permeselectivity toward unbranched aliphatic paraffins vs. branched and cyclic paraffins, can be used.

On-Board Fuel Reforming

Disclosed herein are systems and methods for optimizing the performance of an ICE by altering the RON or CN value of fuel, and additionally generating $H_2$ and combining $H_2$ with the fuel. Combing a fraction of $H_2$ in combination with gasoline or diesel fuels before injection into an ICE can be beneficially increase engine performance and reduce harmful emissions. For gasoline-fueled spark ignition engines, addition of $H_2$ can improve overall engine efficiency, lower hydrocarbon and $NO_x$ emissions, and smooth engine operation by reducing cycle-to-cycle variations of cylinder pressure. The benefits for direct-injection spark ignition include faster and more stable combustion, and reduction in the emission of particulate matter. As desired, $H_2$ can be added to non-diesel fuels such as gasoline and natural gas to promote fuel auto-ignition.

$NO_x$ emissions from diesel-powered engines are often relatively low compared to NO, emissions generated during spark ignition (e.g., from gasoline-powered engines). However, the presence of a large excess of oxygen in diesel exhaust means that the $NO_x$+CO reaction, which is the key pathway for NO, reduction used on gasoline-fueled vehicles, becomes much less favorable as the CO is consumed by direct reaction with 02. For diesel-fueled compression ignition engines, the presence of $H_2$ can obviate the '$NO_x$-particulate tradeoff' and decrease both pollutants simultaneously.

The availability of $H_2$ on board a vehicle also enables a hybrid after treatment process to be operated, by creating a localized highly reducing atmosphere that allows $NH_3$ to be formed in situ during the fuel-rich regeneration of a NO, trap. The $NH_3$ can then act as a selective NOx reductant. For certain catalysts, such as silver for hydrocarbon-SCR, $H_2$ can play a major role to sustain its initial high activity by preventing the self-poisoning effect of surface nitration and inhibiting the dehydrogenation and cyclisation of adsorbed hydrocarbons.

Figure 9:
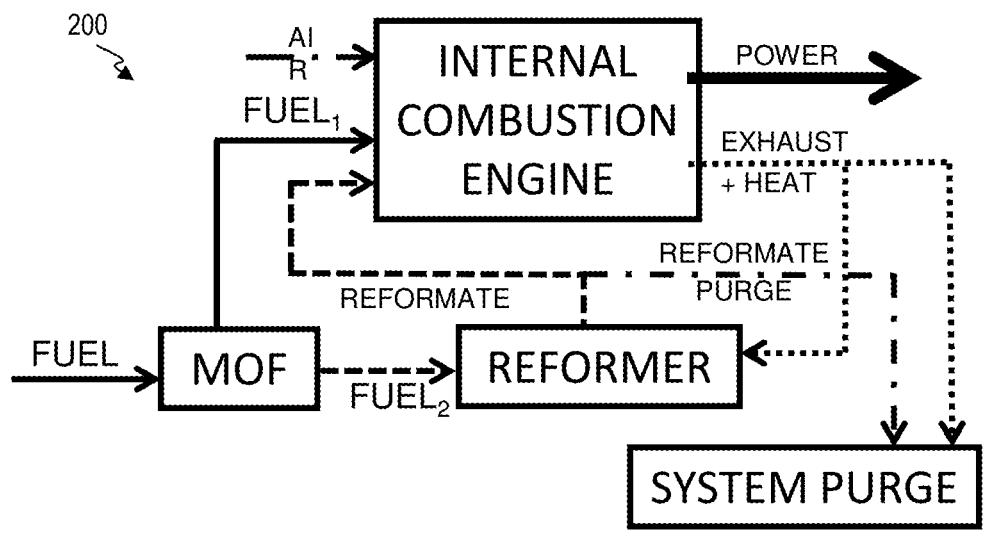
FIG. 9 illustrates a schematic view of a system and method for optimizing the performance of an ICE by generating $H_2$, according to one or more embodiments.

FIG. 9 illustrates a system and method 200 for optimizing the performance of an ICE by generating $H_2$ and injecting the $H_2$ into the ICE in combination with, or in series with, fuel. Additionally, system and method 200 further optimize performance of the ICE by separating a fuel into two or more streams. System and method 200 can be performed on-board a vehicle. System and method 200 comprises contacting a fuel with an MOF, and separating the fuel into a first fuel stream (Fuel$_1$) and a second fuel stream (Fuel$_2$). In some embodiments, fuel can comprise gasoline and/or diesel. Fuel can be supplied by a fuel source, such as a fuel tank. Fuel can contact the MOF in a liquid state, a gaseous state, or combinations thereof. Suitable MOFs will be described below. In some embodiments, separating occurs by the MOF selectively sorbing one or more constituents of the fuel, and subsequently desorbing the selectively sorbed one or more constituents to form a first fuel stream or a second fuel stream. Sorption can include one or more of adsorption and desorption. In some embodiments, separating occurs by the MOF structure, in the form of a membrane or packed bed or column, selectively allowing one or more fuel constituents to permeate the MOF structure. Suitable MOFs generally have very rigid structures, which are capable of maintaining structural stability over a number of sorption/desorption cycles, and/or over a high volume of constituent permeation. In some embodiments, suitable MOFs will have aperture sizes between about 0.4 nm and about 0.6 nm, between about 0.45 and about 0.55 nm, or between about 0.4 and 0.5 nm. In some embodiments, a suitable MOF aperture size can be determined based on the type of fuel being separated. For example, diesel fuel separation depends on the separation of aliphatic n-paraffins, and accordingly a suitable pore aperture can be up to about 0.49 nm, about 0.5 nm, or about 0.51 nm. Conversely, gasoline fuel separation depends on the separation of iso-paraffins from n-paraffins, and additionally or alternatively di-branched paraffins from mono-branched paraffins. Accordingly, a suitable pore aperture for MOFs used in gasoline separation, the range of desirable aperture can be broader, for example about 0.5 nm to about 0.6 nm.

The MOF can separate the fuel based on the degree of branching of the fuel constituent isomers. Accordingly, the MOF can separate the fuel based on RON value. MOFs can separate fuel constituent isomers of butanes, pentanes, hexanes, heptanes, octanes, nonanes and decanes. In one embodiment, the first fuel stream has a higher RON value than the second fuel stream. In one embodiment, the second fuel stream has a higher RON value than the first fuel stream.

The first fuel stream can then be injected into an ICE in combination with air, wherein the first fuel stream is combusted, thereby generating power and heated exhaust. Air can comprise ambient air, or a mixture of one or more of oxygen, nitrogen, and carbon dioxide. Heated exhaust can be directed to one or more of a system purge and a reformer. Exhaust can be treated before entering the reformer. For example, one or more of heat, CO, and CO$_2$ can be transferred from the exhaust sent to the system purge to the exhaust sent to the reformer. System purge can comprise an exhaust to atmosphere. System purge can comprise a storage vessel. For example, a storage vessel can collect one or more of H$_2$ or CO$_2$. System purge can comprise a combination of exhaust to atmosphere and a storage vessel.

A portion of the second fuel stream can optionally be directed to storage. Fuel in storage can optionally be injected into the ICE as a supplemental fuel stream. At least a portion of the second fuel stream can be directed to the reformer in combination with at least a portion of the heated exhaust. Onboard reforming techniques can fall into one or more of the following general categories: a) Steam Reforming, b) Partial Oxidation, c) Thermal Dissociation, d) Exhaust-Gas Reforming.

Through the recovery of waste heat, exhaust gas reforming can improve fuel economy and lower CO$_2$ and other polluting emissions of an ICE. Specifically, an exhaust gas reformer catalyzes endothermic reactions, such as wet and dry reforming, and provides a chemical mechanism for heat recovery. Steam reforming, or wet reforming, is useful in improving fuel heating value due to the endothermic nature of the process, as shown in Equation (1):

$$C_8H_{18}+8H_2O \rightarrow 8CO+17H_2, \Delta H_{298}=+1275 \text{ kJ mol}^{-1} \quad (1)$$

It is usually proposed that this energy requirement might be met by the reclamation of otherwise wasted energy by using heat-exchangers. In steam reforming, the required quantities of steam or/and thermal energy are supplied directly by hot engine exhaust gases. Dry reforming uses exhaust as a source of heat and co-reactants (i.e., CO$_2$) in the conversion of some of the primary fuel into reformate over a supported metal catalyst, as shown in Equation (2):

$$C_8H_{18}+8CO_2 \rightarrow 16CO+9H_2, \Delta H_{298}=+1604 \text{ kJ mol}^{-1} \quad (2)$$

Conversely, partial oxidation is attractive as a means of producing H$_2$-rich gaseous fuels without the need for any external supply of energy, as the reaction is itself exothermic as shown in Equation (3):

$$C_8H_{18}+4O_2 \rightarrow 8CO+9H_2, \Delta H_{298}=-660 \text{ kJ mol}^{-1} \quad (3)$$

Unfortunately, the process consequently has a thermal efficiency of around 80%, implying a reduction in fuel heating value of around 20% across the reformer.

A representative (complete) combustion reaction is provided in Equation (4):

$$C_8H_{18}+25/2O_2 \rightarrow 8CO_2+9H_2O, \Delta H_{298}=-5100 \text{ kJ mol}^{-1} \quad (4)$$

Incomplete combustion reactions will generate CO as an additional reaction product. In equations (1)-(4), the respective reactions are simplified by representing fuel as octane, and it should be understood that one or more various hydrocarbons, branched or unbranched, can additionally or alternatively comprise the fuel portion of each respective reaction.

In case of diesel reforming, a common catalyst is a bi-metallic Pt—Rh supported on ceria-zirconia, but its ability to catalyze wet reforming is inhibited by the presence of sulfur in the fuel.

By using a more sulfur-tolerant support material and by excluding Pt, which oxidizes exhaust SO$_2$ to SO$_3$ (the gas-phase species that accelerates sulfation of the support), a slightly less active but also less sulfur-sensitive catalyst can be designed.

After the second fuel stream and heated exhaust are directed to the reformer, reformate comprising H$_2$ is generated by one of the above discussed methods. The reformate comprising H$_2$ can be injected into the ICE in combination with the first fuel stream and or the second fuel stream. In some embodiments, reformate is processed before injection into the ICE in order to increase the concentration of H$_2$. Such a system and method advantageously increases ICE performance by providing a first fuel stream having a higher RON value or CN value, and utilizing the second fuel stream to generate H$_2$ which can subsequently be injected into the ICE to increase efficiency and reduce polluting emissions such as one of more of NO$_x$ compounds, CO, and CO$_2$.

System and method 200 can optionally comprise a reformate purge. Reformate can have the same composition as reformate purge. In some embodiments, reformate purge comprises treated reformate. For example, reformate purge can comprise reformate which has been treated to remove H$_2$, CO, or CO$_2$.

In a specific embodiment, system and method 200 can selectively direct 2,3-dimethylbutane and 2,2-dimethylbutane into the first fuel stream to increase engine performance, and selectively direct monobranched hexane isomers and n-hexane into the second fuel stream. In this specific embodiment, an MOF based membrane with high permeselectivity toward mono-branched and n-paraffins vs. di-branched paraffins, can be used. In this specific embodiment, an MOF based membrane with high permeselectivity toward mono-branched and n-paraffins vs. di-branched paraffins, can be used. The n-paraffins together with exhaust gas resulting from combustion of the di-branched paraffins will be directed toward the reformer.

Figure 10:
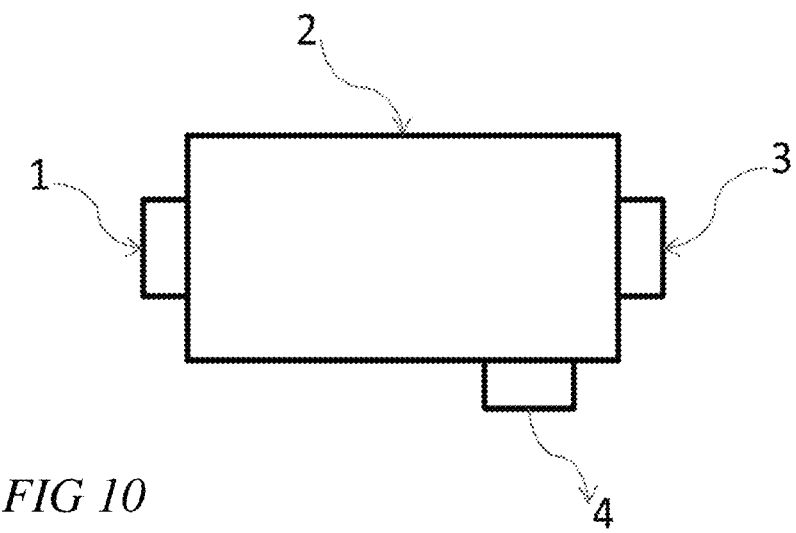
FIG. 10 illustrates a schematic view of a device using one or more MOFs to separate hydrocarbons, according to one or more embodiments.

FIG. 10 illustrates a schematic view of a device using one or more MOFs to separate hydrocarbons (i.e., fuel) into different sizes. In FIG. 10, 1 is a gas flow inlet, 2 is a housing including MOF (not shown), 3 is a gas outlet and 4 is a gas outlet. Hydrocarbons of different sizes can enter the housing through inlet 1, and MOF can separate the hydrocarbons based on their sizes and/or molecular structures. After separation, gas of one size and/or structure can exit through outlet 3 and gas of a second size and/or structure can exit through outlet 4.

Examples of Suitable MOFs

An example of an MOF suitable for the systems and methods described herein is an Fcu-MOF. Examples of rare earth fcu-MOF compositions and methods of synthesis can be found in co-owned U.S. patent application Ser. No. 14/019,511, entitled "Tunable Rare-Earth FCU-Metal-Organic Frameworks", filed Sep. 5, 2013, the disclosure of which is herein incorporated by reference in its entirety.

The metal organic framework composition can comprise $M_6(OH)_{8-x}O_x(R_1COO)_{8-y}(R_2CN_4)_y(H_2O)_z$, wherein x can be an integer that ranges from 0 to 8, wherein y can be an integer that ranges from 0 to 8, wherein z can be an integer that ranges from 0 to 6, wherein $R_1$ can include an aryl, a heteroaryl, a carbocyclyl, or a heterocyclyl, and wherein $R_2$ can include an aryl, a heteroaryl, a carbocyclyl, or a heterocyclyl. M can be selected from the group consisting of Yttrium, Lanthanum, Cerium, Praseodymium, Neodymium, Samarium, Europium, Gadolinium, Terbium, Dysprosium, Holmium, Erbium, Thulium, Ytterbium and Lutetium, The metal organic framework composition can comprise $M_9(OH)_{11-x}O_xL$, wherein x can be an integer that ranges from 0 to 11, wherein M can be a metal ion selected from the group consisting of Yttrium, Lanthanum, Cerium, Praseodymium, Neodymium, Samarium, Europium, Gadolinium, Terbium, Dysprosium, Holmium, Erbium, Thulium, Ytterbium and Lutetium; and wherein L can be a component that can associate with the metal ion. L can include a carboxylate group. L can include a tetrazole group. L can further associate with a compound. The compound can includes include $H_2O$, Dimethylformamide (DMF), dimethylamine (DMA), Dimethyl Ammonium or formate.

L can include $(RCOO)_{18-y-z}(CN_4)_y \cdot R'_z$, wherein y can be an integer that ranges from 0 to 18, wherein z can be an integer that ranges from 0 to 6, wherein R can include an aryl, a heteroaryl, a carbocyclyl, or a heterocyclyl, and wherein $R'_z$ can include a coordinating ligand. The coordinating ligand can include $H_2O$, Dimethylformamide (DMF), dimethylamine (DMA), dimethylammonium, or formate.

A metal organic framework can include a molecular building block. A molecular building block composition can include a metal ion component, and a ligand component including a core including at least one anionic group associated with the metal ion component and the core, wherein the metal ion component and the ligand can associate to form a 4, 6, 8, 10, 12, 14, or 18 connected cluster. The ligand component can include at least two anionic groups associated with the metal ion component. The anionic binding groups can be oriented 180 degrees from each other. The anionic binding groups can be oriented 120 degrees from each other.

The core can include an aryl, a heteroaryl, a carbocyclyl, or a heterocyclyl. The core can include three anionic groups. The core can include four anionic groups. The molecular building block composition can include an oxo component. The oxo component can include a hydroxide group. The oxo component can include an oxide group. The oxo component can include a hydroxide group and an oxide group. The ligand component can include a carboxylate group. The ligand component can include a tetrazole group. The ligand component can include a carboxylate group and a tetrazole group.

The molecular building block can include a hexanuclear cluster. The metal organic framework can comprise a nonanuclear cluster. The metal organic framework can include a 12-connected net; a 4, 12-connected net; a 4, 8-connected net; a 6-connected net; a 3, 8-connected net; an 8-connected net; a 3, 18-connected net, or a 6, 12-connected net.

A molecular building block composition can include $L9_3M_6(OH)_8$, wherein M can be selected from the group consisting of Yttrium, Ytterbium and Terbium. A molecular building block composition can include $L10_3M_6(OH)_8$, wherein M can be selected from the group consisting of Yttrium and Terbium.

A metal organic framework composition can include oxybis(benzoic) acid and a rare earth metal; benzenetrisbenzoic acid and a rare earth metal; 5-((4-carboxybenzyl)oxy) isophthalic acid and a rare earth metal; [1,1'-biphenyl]-3,4', 5-tricarboxylic acid and a rare earth metal; 5-(4-carboxy-3-nitrophenoxy)isophthalic acid and a rare earth metal; thiophen dicarboxylic acid and a rare earth metal; Pyridine carboxylic acid and a rare earth metal; or thiophene-2,5-dicarboxylic acid and a rare earth metal.

An example of MOFs suitable for the systems and methods described herein are Zeolite-like MOFs (ZMOFs). ZMOFs represent a unique subset of MOFs that are topologically related to the pure inorganic zeolites and exhibit similar properties: (i) tunable apertures and cavities, (ii) chemical stability, (iii) ion exchange capability that make it possible to control and tune extraframework cations for the enhancement of interaction toward specific guest molecules, (iv) tunable inorganic and organic components that permit facile alteration of pore size and/or organic functionality.

A ZMOF can be anionic, and can have a sodalite topology. The z ZMOF can include a linker and a metal. The metal can include Indium, Yttrium, or Cadmium, or a combination thereof. The linker can include an imidazole or pyrimidine moiety. A method for preparing a zeolite-like metal-organic framework membrane can include contacting a substrate with a solution mixture of carboxylic acid, an imidazole, a metal salt, and a nitric acid to form a zeolite-like metal-organic framework membrane.

A defect-free ZMOF thin-film membrane, with a pure phase sodalite topology (sod-zMOF(Im)) can be fabricated and used for fuel upgrading and reforming. This membrane showed a unique CO2 separation properties for purification of $H_2$ and $CH_4$ due mainly to the combination of adsorption effect (charged framework) and the small window aperture of the sod-zMOF (4.1 Å). Because of the small windows aperture (4.1 Å) of sod-zMOF(Im) that allows the permeation/adsorption of n-paraffins (for example n-hexane (3.8-4.3 Å)), this membrane is an ideal starting materials to target molecular sieving of di-branched paraffins (such as 2,3 dimethylbutane (5.6 Å) and 2,2 dimethylbutane (6.2 Å)) from mono-branched and n-paraffins targeting gasoline upgrading to high RON numbers.

An example of an MOF suitable for the methods described herein is an ana-ZMOF. ana-ZMOFs have an ana topology are characterized by the formula $[M^{III}(4, 5\text{-imidazole dicarboxylic acid})_2X(\text{solvent})_a]_n$ wherein $M^{III}$ comprises a trivalent cation of a rare earth element, X comprises an alkali metal element or alkaline earth metal element, and n represents the number of molecular building blocks. In some embodiments, $M^{III}$ comprises one or more of a trivalent cation of a rare earth element, including cerium ($Ce^{3+}$), dysprosium ($Dy^{3+}$), erbium ($Er^{3+}$), europium ($Eu^{3+}$), gadolinium ($Gd^{3+}$), holmium ($Ho^{3+}$), lanthanum ($La^{3+}$), lutetium ($Lu^{3+}$), neodymium ($Nd^{3+}$), praseodymium ($Pr^{3+}$), promethium ($Pm^{3+}$), samarium ($Sm^{3+}$), scandium ($Sc^{3+}$), terbium ($Tb^{3+}$), thulium ($Tm^{3+}$), ytterbium ($Yb^{3+}$), or yttrium ($Y^{3+}$).

In some embodiments, the ligand is a heterofunctional ditopic ligand, such as 4,5-imidazole dicarboxylic acid (ImDC). ImDC possesses two N- and O-hetero-chelating moieties with a potential angle of 144°, as directed by the metal-nitrogen coordination. In some embodiments the ligand is one or more of 1H-Imidazole-2-carboxylic acid, 2,7-diaza-antracene-1,8-dicarboxylic acid, pyrimidine-4,6-dicarboxcylic acid, pyridine-2,5-dicarboxylic acid, or 2,7-diaza-anthracene-3,6-dicarboxylic acid; and/or benzene-1,2,4,5,tetracarboxylic acid, naphthalene-2,3,6,7-tetracarboxylic acid, anthracene-2,3,6,7-tetracarboxylic acid.

In some embodiments, X comprises one or more of an alkali metal element, including lithium, sodium, potassium, rubidium, caesium, or francium. In other embodiments, X comprises one or more of an alkaline earth metal element, including beryllium, magnesium, calcium, strontium, barium, or radium.

In some embodiments, the solvent can be $H_2O$, N,N-dimethyl formamide (DMF), ethanol, 4,4;-trimethylene-dipiperidine, or 1,2-diaminocyclohexane. In other embodiments, the solvent guest molecules are evacuated. Consequently, a can vary down to zero, without any change in the definitional framework of the ana-ZMOF.

In particular, ana-ZMOFs can be used to kinetically separate linear paraffins from branched paraffins. Single component adsorption isotherms of linear paraffins and branched paraffins illustrate that the adsorption of linear paraffins is nearly double the adsorption of branched paraffins. In addition, an analysis of the kinetics of sorption on ana-ZMOF shows that linear paraffins are adsorbed at a much faster rate than branched paraffins. Consequently, ana-ZMOF is the ideal candidate material for kinetically separating linear paraffins from branched paraffins.

In some embodiments, the separation of linear paraffins from branched paraffins is kinetic-based, as opposed to equilibrium-based. In some embodiments, the separation is based on a difference in kinetic diameter and pore aperture size, wherein paraffins with a kinetic diameter that is less than the pore aperture diameter diffuse and/or adsorb on the ana-ZMOF and paraffins with a kinetic diameter that is greater than the pore aperture diameter remain in the bulk phase. In some embodiments, ana-ZMOF is used to separate paraffins with a kinetics diameter greater than about 4.2 Å to 5 Å. In some embodiments, the separation is based on a difference in time that it takes a paraffin to reach equilibrium for sorption on an ana-ZMOF, wherein the time it takes a branched paraffin to reach equilibrium is much greater than the time it takes a linear paraffin to do the same. In some embodiments, the separation is based on both a difference in kinetic diameter and/or pore size, and a difference in equilibrium times.

An example of an MOF suitable for the methods described herein is a fumarate-lanthanide fcu-MOF, or fcu-fumaric MOFs. fcu-fumaric MOFs can be characterized by $RE_6O_4(OH)_4(\text{fumarate})_6(\text{solvent})_x$, and can be designed and synthesized to have pore apertures of about 4.3-3.5 Å. Single component adsorption isotherms of linear and branched paraffins were investigated and showed significant and extremely fast adsorption of linear paraffins (such as butane, pentane, etc.) with type I adsorption isotherm. No adsorption of branched paraffins (isobutane, isopentane) was observed Fumarate-lanthanide fcu-MOFs are ideal for sieving aliphatic paraffins from branched and cyclic paraffins, including the use of both adsorption and membrane technologies. Any linear ditopic ligand with one or more carboxylates, and with a similar size or shorter than a fumarate, can also be utilized. One example, is a squarate. The particular high chemical and thermal stability of this class of materials combined with the easy pore (and aperture) size tunability provides avenues for challenging paraffin/branched paraffin separation.

MOF compositions of the present embodiments include MOFs based on a series of isoreticular structures. These unique materials are built up from an original lanthanide based hexanuclear cluster connected by homo/heterofunctional ditopic ligand, which exhibit outstanding properties in term of separation of traces $CO_2$ from, $CH_4$, $O_2$, $N_2$ containing gas streams.

The use of reticular chemistry approach has been successfully implemented to purposefully fine tune the pore size of a rare earth (RE) fcu-platform. The purposeful selection of organic building block, such as fumaric acid or squaric acid, allows for a RE ($Tb^{3+}$ and $Y^{3+}$) fcu MOF analogue that displays unprecedented substantially complete to complete sieving of branched paraffins from linear paraffins. This newly isolated MOF molecular sieve has a crystallographically determined window aperture of about 3.8 Å, which was found to represent, in this case, the crystallographic cut-off window size allowing a substantially complete to complete sieving of branched paraffins from linear paraffins. A combination of single and mixed gas/vapor adsorption and calorimetric studies confirm that n-pentane and n-butane were adsorbed into the pores of the fum-fcu-MOF with fast adsorption kinetics, while no adsorption was observed for mono-branched isopentane and isobutane.

As used herein, "fumaric acid" refers to a chemical compound of formula $HO_2CCH=CHCO_2H$:

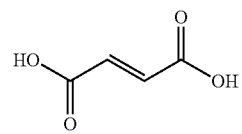

The salts and esters of which are referred to as "fumarates".

As used herein, "squaric acid" or "quadratic acid" refers to a chemical compound of formula: $C_4H_2O_4$

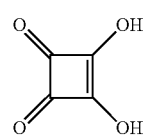

The salts and esters of which are referred to as "squarates".

An example of an MOF suitable for the methods described herein is a SIFSIX MOF. SIFSIX MOFs can be identified generally as SIFSIX-n-M, wherein n is at least two, and M can comprise Cu, Zn, Co, Mn, Mo, Cr, Fe, Ca, Ba, Cs, Pb, Pt, Pd, Ru, Rh, and Cd. The SIFSIX-n-M MOF class is isoreticular across its metal analogues (i.e., each M analogue has the same framework topology) and is characterized by periodically arrayed hexafluorosilicate (SIFSIX) octahedral pillars. SIFSIX-n-M MOFs have many desirable characteristics, including tunable pore sizes, which lend the various analogues well to a number of industrial applications.

Ligands for SIFSIX MOFs can comprise a polydentate, or poly-functional ligand, such as a bi-functional ligand, a tri-functional ligand, or ligands with four or more functional sites. In some embodiments, a ligand can comprise an N-donor linker. Ligands can comprise a poly-functional ligand. In some embodiments, a ligand can comprise a plurality of N-donor functional groups. In some embodiments, a ligand can comprise a monocyclic or polycyclic group structure, wherein the cyclic groups can be aromatic or non-aromatic. In some embodiments, a ligand can comprise a nitrogen-containing monocyclic or polycyclic group structure. In some embodiments, a ligand can comprise a nitrogen-containing heterocyclic ligand, including pyridine, pyrazine, pyrimidine, pyridazine, triazine, thiazole, oxazole, pyrrole, imidazole, pyrazole, triazole, oxadiazole, thiadiazole, quinoline, benzoxazole, benzimidazole, and tautomers thereof.

Example 1: Steric Separation of Aliphatic n-Paraffins from Aliphatic Iso-Paraffins Using Rare-Earth Fcu-MOF An isoreticular rare earth (RE) fcu-MOF comprising a short fumarate (fum) ligand was used to separate aliphatic n-paraffins from aliphatic iso-paraffins. The RE-fcu-MOF platform was synthesized in the presence of fumaric acid to yield 12-connected RE ($Y^{3+}$ and $Tb^{3+}$) fumarate based fcu-MOF with contracted aperture sizes. Both the Y and Tb analogues were characterized by classical octahedral and tetrahedral cages with the diameter of the largest spheres that can fit into these cages (taking into account the Van der Waals surface) are about 7.6 and 5.2 Å, respectively. In particular, the Y anaolgue crystallized in a cubic crystal system with Pn-3 space group with unit cell parameter a=18.5353(9) Å. Each yittrium cation ($Y^{3+}$) was surrounded by four oxygen atoms from four $\mu_3$-OH groups, four oxygen atoms from carboxylate groups belonging to three crystallographically independent fumarate ligands, and one terminal water molecule. The adjacent Y ions are bridged via $\mu_3$-OH and deprotonated carboxylate groups in a bis-monodentate fashion giving rise to the 12-coordinated hexanuclear molecular building block (MBB), $[Y_6(\mu_3\text{-OH})_8(O_2C—)_{12}]$. Each hexanuclear MBB is connected to 12 fumarate ligands to generate a 3-periodic MOF. The resultant crystal structure confirmed that the topology of the Y analogue corresponds to the expected fcu net, the only 12-connected edge transitive net. The hexanuclear cluster $[Y_6(\mu_3\text{-OH})_8(O_2C—)_{12}]$ MBBs, where the carbons atoms of the carboxylate moieties act as points of extension, coincide with the cuboctahedron vertex figure of the fcu net.

Figure 11A:
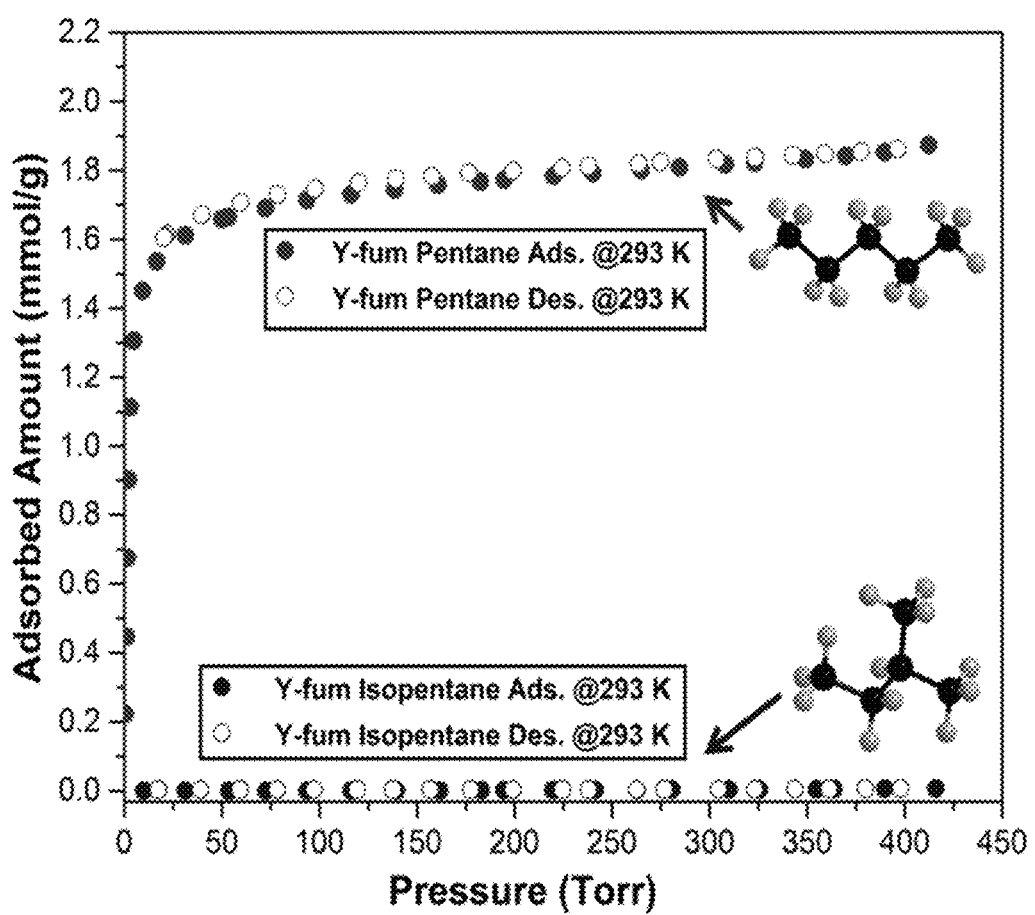
FIG. 11A illustrates n-pentane and isopentane sorption isotherms at 393 K for the Y-fum-MOF, according to one or more embodiments.
Figure 11B:
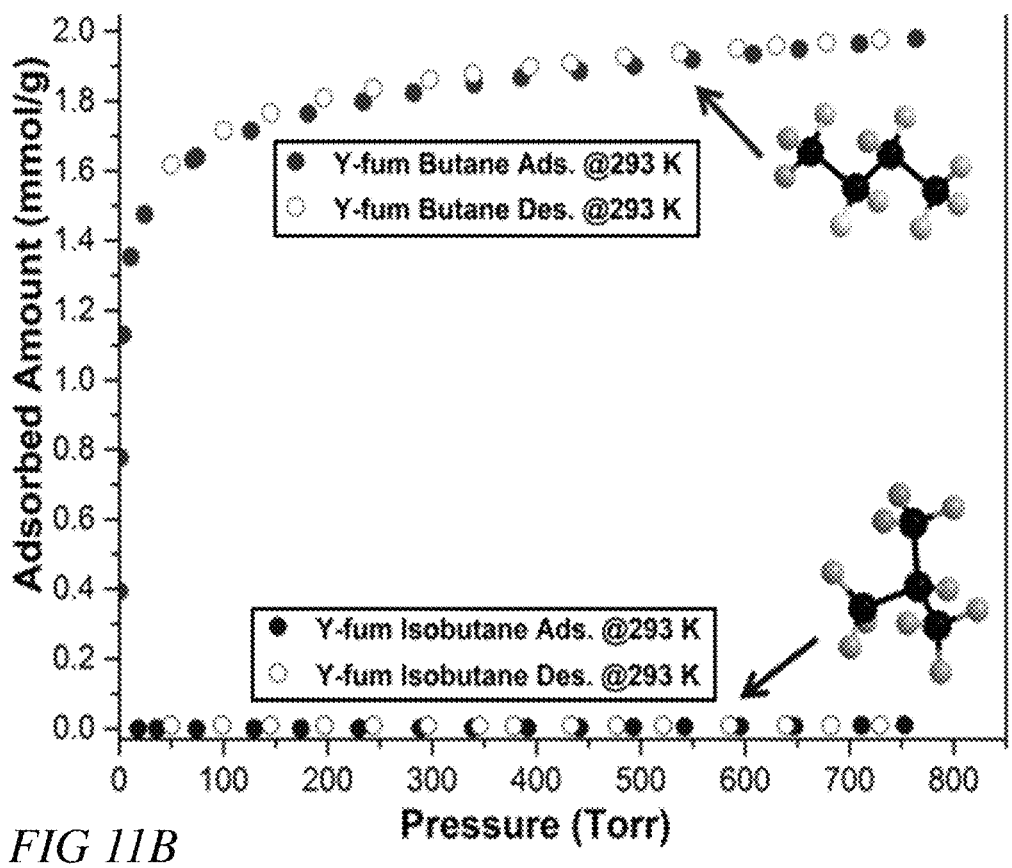
FIG. 11B illustrates n-butane and isobutene sorption isotherms at 393 K for the Y-fum-MOF, according to one or more embodiments.

The choice of fumaric acid as ligand permits the precise control of the access to the cages through triangular windows apertures of ca. 4.7 Å. Such window apertures are advantageously slightly larger than most of linear paraffins (n-butane≈4.3 Å) and shorter that most of mono and dibranched paraffins (iso-butane≈5 Å). Accordingly, the Y and Tb analogues exhibited a perfect cut-off aperture size for the total separation of n-pentane-iso-pentane, n-butane-isobutane and paraffins-branched paraffins in general. FIG. 11A illustrates pentane and isopentane sorption isotherms at 393 K for the Y-fum-MOF. FIG. 11A illustrates n-pentane and isopentane sorption isotherms at 393 K for the Y-fum-MOF. FIG. 11B illustrates n-butane and isobutene sorption isotherms at 393 K for the Y-fum-MOF.

Figure 12A:
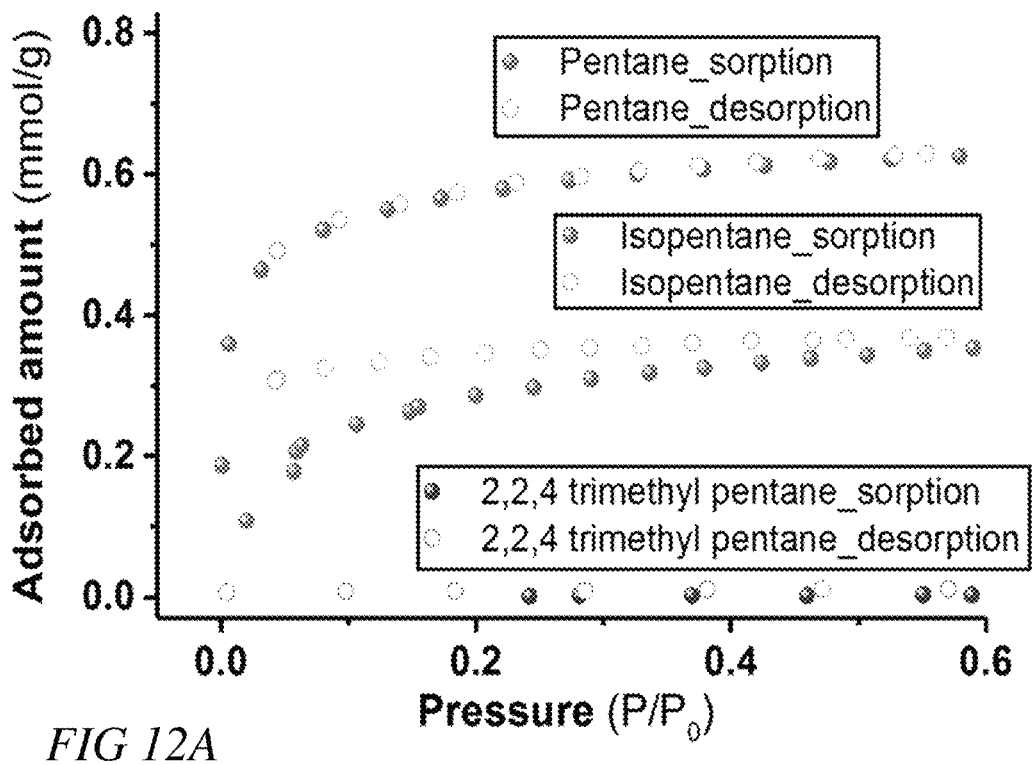
FIG. 12A illustrates a graphical view of single-component adsorption isotherms for pentane, isopentane, and 2,2,4-trimethylpentane on a zeolite-like metal-organic, according to one or more embodiments.

Example 2: Kinetic Separation of Aliphatic n-Paraffins from Aliphatic Iso-Paraffins Using Ana-ZMOF FIG. 12A illustrates a graphical view of single-component adsorption isotherms for pentane, isopentane, and 2,2,4-trimethylpentane on a zeolite-like metal-organic framework with ana topology, indicating the amount of pentane, isopentane, and 2,2,4-trimethylpentane adsorbed with changes in pressure at 20° C. With respect to the separation of n-pentane from isopentane, FIG. 12A illustrates that the adsorption of pentane on an ana-ZMOF is almost double the adsorption of isopentane. With respect to 2,2,4-trimethylpentane, FIG. 12A illustrates that 2,2,4-trimethypentane was experimentally not observed adsorbing onto or diffusing into the pores of ana-ZMOF. In some embodiments, ana-ZMOF can be used as a molecular sieve to separate high octane rating gasoline components from low octane rating gasoline components comprising mono-branched paraffins and linear paraffins, with infinite selectivity.

Figure 12B:
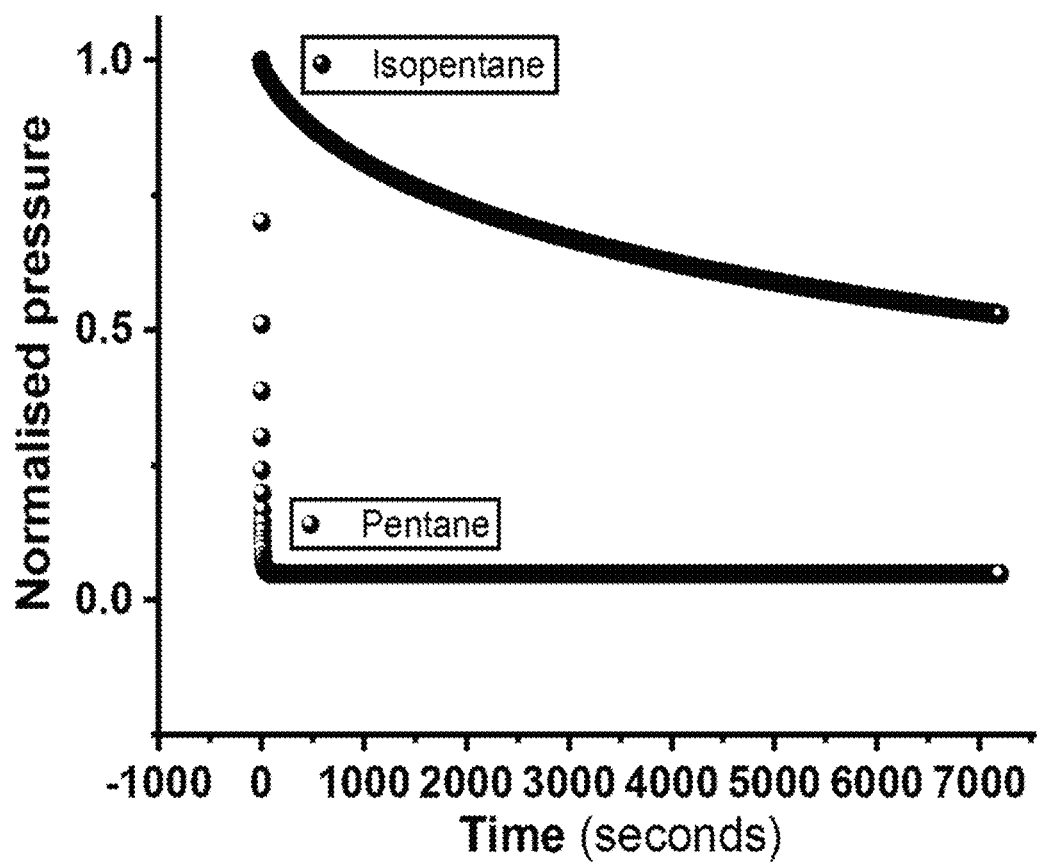
FIG. 12B illustrates a graphical view of the adsorption of pentane and isopentane on a zeolite-like metal-organic framework, according to one or more embodiments.

FIG. 12B illustrates a graphical view of the adsorption of pentane and isopentane on a zeolite-like metal-organic framework with ana topology, indicating the normalized pressure of pentane and isopentane as a function of time at 20° C. More specifically, FIG. 12B illustrates that an analysis of the kinetics of sorption clearly show that pentane is adsorbed much faster than isopentane, with a time of greater than 5000 seconds for the sorption of isopentane to reach equilibrium.

What is claimed is:

1. A composition, comprising:
a metal-organic framework composition with ana topology characterized by the formula $[M^{III}(4, 5\text{-imidazole dicarboxylic acid})_2X(\text{solvent})_a]_n$ wherein $M^{III}$ comprises a trivalent cation of a rare earth element, X comprises one or more alkali metal elements or one or more alkaline earth metal elements, solvent comprises a guest molecule occupying pores, a is at least 1, and n is at least 1.

2. The composition of claim 1, wherein $M^{III}$ includes one or more of any one of the following trivalent cations of a rare earth element: $Ce^{3+}$, $Dy^{3+}$, $Er^{3+}$, $Eu^{3+}$, $Gd^{3+}$, $Ho^{3+}$, $La^{3+}$, $Lu^{3+}$, $Nd^{3+}$, $Pr^{3+}$, $Pm^{3+}$, $Sm^{3+}$, $Sc^{3+}$, $Tb^{3+}$, $Tm^{3+}$, $Yb^{3+}$, or $Y^{3+}$.

3. The composition of claim 1, wherein X is lithium, sodium, potassium, rubidium, cesium, francium, beryllium, magnesium, calcium, strontium, barium, or radium.

4. The framework of claim 1, wherein the metal-organic framework composition with ana topology is anionic.

5. The composition of claim 1, wherein the pore sizes of the metal-organic framework composition with ana topology tunable to within a range of less than about 0.5 Å.

6. The composition of claim 1, wherein the pore sizes of the metal-organic framework composition with ana topology are tuned to about 4.2 Å to 5.0 Å.

7. The composition of claim 1, wherein the metal-organic framework composition with ana topology is one or more of a thin film membrane and a zeolite molecular sieve.

8. The composition of claim 1, wherein the metal-organic framework composition with ana topology is an adsorbent for separating paraffins by size.

9. A method of separating paraffins, comprising:
contacting a metal-organic framework with ana topology with a flow of paraffins, and
separating the paraffins by size,
wherein the metal-organic framework with ana topology is characterized by the formula $[M^{III}(4, 5\text{-imidazole dicarboxylic acid})_2X(\text{solvent})_a]_n$ wherein $M^{III}$ comprises a trivalent cation of a rare earth element, X comprises one or more alkali metal elements or one or more alkaline earth metal elements, solvent comprises a guest molecule occupying pores, a is at least 1, and n is at least 1.

10. The method of claim 9, wherein separating paraffins by size includes separating isoparaffins from paraffins.

11. The method of claim 9, wherein separating paraffins by size includes separating linear paraffins from branched paraffins.

12. The method of claim 9, wherein n-pentane is kinetically separated from isopentane.

13. The method of claim 9, wherein separating paraffins by size includes separating one or more of linear paraffins and mono-branched paraffins from 2,2,4-trimethylpentane.

14. The method of claim 9, wherein $M^{III}$ includes one or more of any one of the following trivalent cations of a rare earth element: $Ce^{3+}$, $Dy^{3+}$, $Er^{3+}$, $Eu^{3+}$, $Gd^{3+}$, $Ho^{3+}$, $La^{3+}$, $Lu^{3+}$, $Nd^{3+}$, $Pr^{3+}$, $Pm^{3+}$, $Sm^{3+}$, $Sc^{3+}$, $Tb^{3+}$, $Tm^{3+}$, $Yb^{3+}$, or $Y^{3+}$.

15. The method of claim 9, wherein X is lithium, sodium, potassium, rubidium, cesium, francium, beryllium, magnesium, calcium, strontium, barium, or radium.

16. The method of claim 9, wherein paraffins with high cetane numbers are separated from paraffins with low cetane numbers.

17. The method of claim 9, wherein paraffins with a kinetic diameter of greater than about 4.2 Å to 5.0 Å are separated from paraffins with a smaller kinetic diameter.

18. The method of claim 9, wherein paraffins with high research octane numbers are separated from paraffins with low research octane numbers.

19. The method of claim 18, wherein the paraffins with low research octane numbers include one or more of linear paraffins and mono-branched paraffins.

* * * * *